United States Patent
Kasinkas et al.

(10) Patent No.: US 6,263,236 B1
(45) Date of Patent: Jul. 17, 2001

(54) NON-OCCLUSIVE EXPANDABLE CATHETER

(75) Inventors: Michael Kasinkas, Plymouth; Robert Ziebol, Blaine, both of MN (US)

(73) Assignee: Illumenex Corporation, Plymouth, MN (US)

( * ) Notice: Subject to any disclaimer, the term of this patent is extended or adjusted under 35 U.S.C. 154(b) by 0 days.

(21) Appl. No.: 09/450,312

(22) Filed: Nov. 29, 1999

(51) Int. Cl.⁷ ............................................. A61N 1/30
(52) U.S. Cl. ............................................................. 604/21
(58) Field of Search .................................. 604/114, 113, 604/21, 96.01, 105–106, 107; 600/439; 606/32, 33, 41, 7, 8, 13–17; 607/80, 88

(56) References Cited

U.S. PATENT DOCUMENTS

| | | | |
|---|---|---|---|
| Re. 34,544 | 2/1994 | Spears | 604/20 |
| 4,878,492 | 11/1989 | Sinofsky et al. | 128/303.1 |
| 5,074,871 | 12/1991 | Groshong | 606/170 |
| 5,188,602 | 2/1993 | Nichols | 604/113 |
| 5,188,635 | 2/1993 | Radtke | 606/14 |
| 5,366,443 * | 11/1994 | Eggers et al. | 604/114 |
| 5,620,438 | 4/1997 | Amplatz et al. | 606/10 |
| 5,632,767 | 5/1997 | Sinofsky | 607/89 |
| 5,637,877 | 6/1997 | Sinofsky | 250/492.1 |
| 5,643,253 | 7/1997 | Baxter et al. | 606/17 |
| 5,649,978 | 7/1997 | Samson | 623/1 |
| 5,700,243 | 12/1997 | Narciso, Jr. | 604/102 |
| 5,797,868 | 8/1998 | Leone | 604/21 |
| 5,824,005 | 10/1998 | Motamedi et al. | 606/15 |
| 5,833,682 | 11/1998 | Amplatz et al. | 606/15 |
| 5,855,565 | 1/1999 | Bar-Cohen et al. | 604/104 |
| 5,876,426 | 3/1999 | Kume et al. | 607/88 |
| 5,964,751 | 10/1999 | Amplatz et al. | 606/15 |
| 6,004,269 * | 12/1999 | Crowley et al. | 600/439 |

* cited by examiner

Primary Examiner—Manuel Mendez
(74) Attorney, Agent, or Firm—Thomas J. Engellenner; Nutter, McClennen & Fish, LLP

(57) ABSTRACT

Non-occluding catheters and methods for delivering energy to a vessel wall without occluding blood flow through the vessel wall are disclosed. In particular, the invention uses an energy distributor connected to an expansion mechanism and a waveguide. The expansion mechanism causes the distributor to come into close proximity with a target region in the vessel wall, while maintaining at least one fluid passageway for blood flow throughout the instrument.

55 Claims, 5 Drawing Sheets

NON-OCCLUSIVE EXPANDABLE CATHETER

BACKGROUND OF THE INVENTION

The technical field of this invention is catheter-based methods and devices for treatment of cardiovascular conditions.

Diseased sites in blood vessels, such as atherosclerotic plaques, aneurysms, stenotic lesions, blocked arteries, and the like, have often been treated using catheters that deliver light, heat or therapeutic agents to the treatment site. Catheters used for this purpose are designed to fit suitably into the lumen of the vessel under treatment.

In U.S. Pat. No. 5,053,033 issued to Clarke, UV radiation is delivered by means of an optical fiber incorporated in a catheter to reduce incidences of restenosis at an angioplasty site. The blood vessel walls are irradiated with UV light during the course of angioplasty procedure, and the effect of the irradiation is to reduce proliferation of smooth muscle cells at this site.

In U.S. Pat. No. Reissue 34,544 issued to Spears et al., therapies are disclosed based on the administration of haematoporphyrin, which is selectively taken up by atherosclerotic plaques. Subsequently, light in the IR range is delivered to the plaque, resulting in the lysis of the plaque. A balloon catheter equipped with a flexible optical fiber is used to deliver the light. When the balloon is inflated, it displaces the opaque blood, allowing transmission of the IR energy through the balloon to the plaque.

In U.S. Pat. No. 5,620,438 issued to Amplatz et al., a balloon catheter is disclosed that causes the radiant energy to exit the catheter in a radial band to treat blood vessel walls. The area of the vessel wall is exposed to the radiant energy in a controlled manner following balloon angioplasty to reduce the tendency of restenosis.

In U.S. Pat. No. 5,797,868 issued to Leone, a photodynamic balloon catheter is used to evenly distribute radiation to the vessel wall. The catheter has a light passing inner tube, a light passing fluid and a light passing inflatable balloon. Light emanating from an optical fiber is reflected through these components to provide uniform illumination within the blood vessels.

Medicaments can also be administered to a subject using catheters. The advantage of using a catheter is that the catheter provides a direct delivery of the medicament to the target site. This minimizes the chance of side effects often encountered by systemic administration of the medicament. In U.S. Pat. No. 5,087,244, issued to Wolinsky et al., a catheter with a flexible balloon having a plurality of minute openings is used to deliver drugs to the vessel. For example, the balloon can be inflated with a heparin solution, and as the walls of the balloon contact the arterial wall, the heparin exits the balloon, directly onto the walls.

However, a serious drawback to using catheters for these types of treatments is that the catheter blocks the flow of blood through the vessel distal to the delivery site, depriving tissue of needed blood. This can cause tissue damage, even when the procedure is performed expediently. Therefore, the amount of time available for drug or light delivery is limited.

The object of this invention is to provide a catheter that can deliver light, heat or a therapeutic agent to a target region in a vessel wall without occluding blood flow in the vessel.

SUMMARY OF THE INVENTION

In general, methods and devices are disclosed for delivering energy and/or therapeutic agents to a target region in a vessel without occluding fluid flow in the vessel.

In one aspect, the invention features a catheter for applying energy to a wall of a vessel without occluding fluid flow. The catheter is typically an elongated hollow instrument having at least one lumen. A waveguide can be disposable within the lumen with the proximal end of such waveguide being adapted to receive energy from an energy source, and a diffuser or distributor disposed of at the distal end of the waveguide constructed to receive energy transmitted from the energy source via the waveguide, and to deliver the energy into a target region of a vessel wall. The invention can further include an expansion mechanism connected to the energy distributor for expanding the instrument at the target region in order to bring the energy distributor into close proximity with the vessel wall while creating at least one fluid passageway through the expanded portion of the instrument.

In one embodiment, the waveguide is a single optical fiber. In another embodiment, the waveguide is a plurality of optical fibers. In a preferred embodiment, the energy distributor is a light distributor. In one embodiment, the light distributor has a single light diffusive tube. In another embodiment, the light diffuser has a plurality of light diffusive tubes. In yet another embodiment, the light diffuser further comprises a light scattering material which directs light to the walls of the light distributor. The light scattering material can further comprise a polymeric material which has light scattering particles dispersed therein. Examples of light scattering particles include, but are not limited to, the group consisting of alumina, silica, and titania compounds and mixtures thereof In another embodiment, the light scattering material is coated on the inner side of the light diffuser. The instrument can further comprises a sheath-like casing that encapsulates the energy-distributing elements.

In another embodiment of the invention, the energy waveguide can be replaced by a medicament conduit which similarly cooperates with an expansion mechanism to provide target administration of a drug or other therapeutic agent to a region of a vessel wall without occluding blood flow. In yet another embodiment, the energy waveguide and medicament conduit can be used in tandem. In another aspect of the invention, various expansion mechanisms are disclosed which bring a portion of the instrument into close proximity with the vessel wall. In one embodiment, the expansion mechanism comprises a flexible spring expander. In another embodiment, the expansion mechanism comprises a coil expander. In yet another embodiment, the expansion mechanism includes a shape-memory material that expands as it is pushed out of a lumen in the instrument. The expansion mechanism may also include a pull wire or push wire or other control mechanism to activate the expansion mechanism from a contracted state to an expanded state.

In another aspect, the invention features a method for delivering energy or medicaments to the walls of a vessel without occluding fluid flow by inserting a catheter having an expansion mechanism into the lumen of the vessel. The catheter having an elongated hollow instrument with at least one lumen, an optional waveguide disposable within the lumen with a proximal end adapted to receive energy, a distributor at the distal end of the waveguide constructed to receive and distribute the energy or medicament to the target region of a vessel wall, and an expansion mechanism for expanding the distal end of the instrument at the target region. The expansion mechanism is activated, thereby expanding the distributor at the target region while creating at least one fluid passageway for blood flow through the diffuser. For photo or thermal therapies, energy can be delivered from an energy source to the interior of the energy distributor via the waveguide and transmitted from the distributor to the target region.

Alternatively, in another aspect, the invention features a method for treating a lesion in a vessel without occluding fluid flow by inserting a catheter into the lumen of a vessel. In this method the catheter is an elongated hollow instrument with at least one lumen, and optionally includes a waveguide disposable within the lumen with a proximal end adapted to receive energy together with an energy distributor at the distal end of the waveguide constructed to receive and distribute the energy to the target region of a vessel wall. Alternatively, the lumen is used to transport a drug or therapeutic agent to a drug dispenser. An expansion mechanism connected to the energy or drug distributor for expanding the distributor at the target region. The target region is irradiated or heated or cooled by an energy source such that the treatment alters the target region, thereby treating the lesion. Alternatively, the lumen may be used to transport saline or other flushing media to the distributor or a dispenser associated therewith, such that the fluid, when dispensed at a target site, can clear blood or other substances that might interfere with energy delivery, if they were otherwise trapped or left between the distributor and the vessel wall.

The lesion can be any lesion requiring treatment. Examples include, but are not limited to, aneurysms and atherosclerotic plaques. In one embodiment, the target region is irradiated with a light source, e.g., UV radiation. In another embodiment, the target region is irradiated with a heat source or a cryogenic source.

In another aspect, the invention features a method for treating a lesion in a vessel without occluding fluid flow by administering a therapeutically effective amount of a photoactivatable therapeutic agent to the subject. Inserting a catheter into the lumen of a vessel. The catheter having an elongated hollow instrument with at least one lumen, a waveguide disposable within the lumen with a proximal end adapted to receive energy, a diffuser at the distal end of the waveguide constructed to receive energy and diffuser the energy to the target region of a vessel wall, and an expansion mechanism connected to the energy diffuser for expanding the diffuser at the target region. The target region is irradiated or heated with an energy source that modulates the therapeutic agent such that the therapeutic agent alters the target region, thereby treating the lesion.

In one embodiment, the therapeutic agent selected from the group consisting of a photoactivatable agent and a thermoactivatable agent. In another embodiment, the step of administering comprises systemically administering the therapeutic agent. In another embodiment, the step or administering comprises locally administering the therapeutic agent.

BRIEF DESCRIPTION OF THE DRAWINGS

A more complete understanding of the present invention and the attendant advantages and features thereof will be more readily understood by reference to the following detailed description when considered in conjunction with the accompanying drawings wherein.

DETAILED DESCRIPTION OF THE INVENTION

Figure 1:
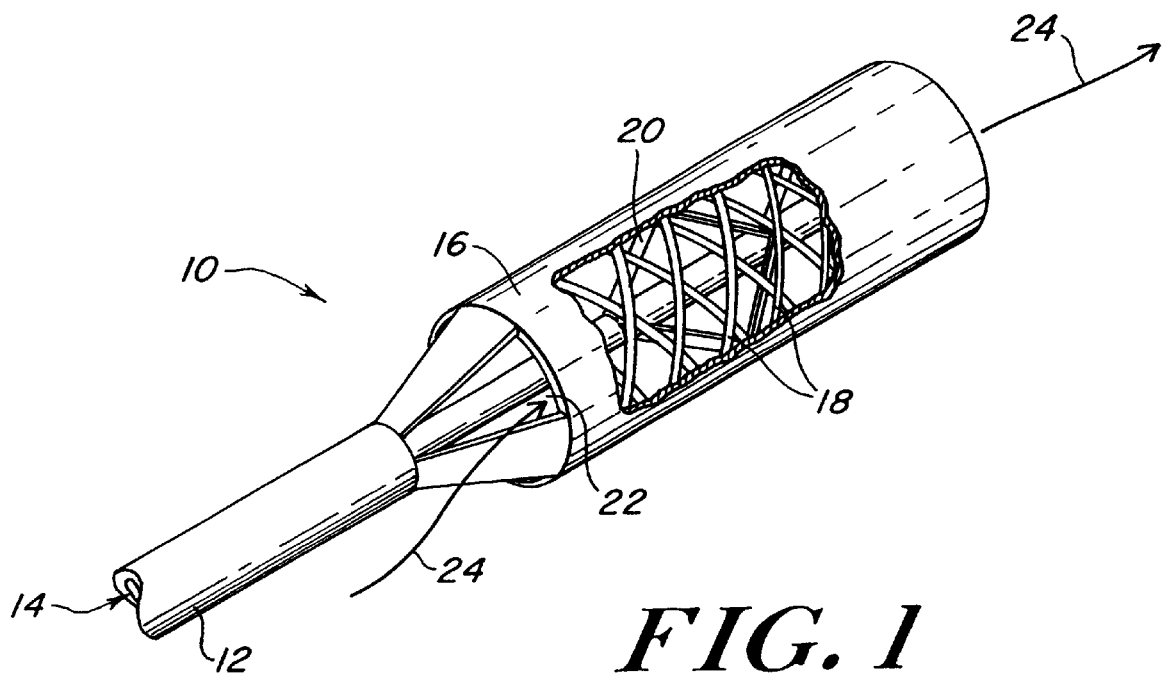
FIG. 1 is a schematic, partially cut-away perspective view of a non-occluding catheter according to the invention.

FIG. 1 shows one embodiment of the non-occluding catheter 10 of the invention. The non-occluding catheter generally comprises a hollow instrument body 12 with at least one lumen 14. At the distal end of the instrument, a sheath casing 16 is disposed, within which is a distributor 18 that, optionally, receives energy from an energy source and transmits the energy to a target region in a vessel wall when the expansion mechanism 20, connected to the distributor 18 expands to bring the distributor into close proximity with the vessel wall. The distributor 18 can also deliver energy by cooling the site. In a cooling embodiment, the waveguide serves to connect the distributor 18 with a cryogenic energy source. The expansion mechanism 20,also creates at least one fluid flow passage 22 that allows unobstructed continuous fluid flow 24.

Figure 2:
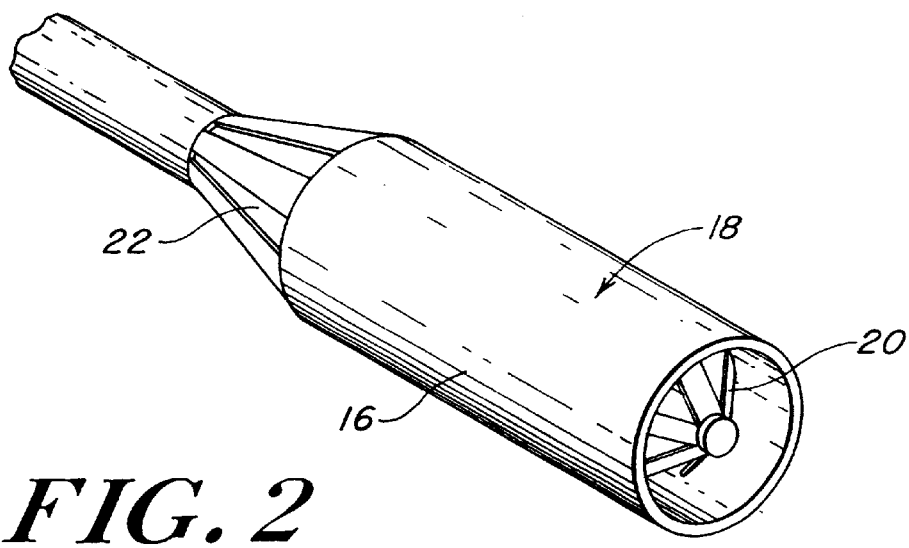
FIG. 2 is a frontal perspective view of a non-occluding catheter of FIG. 1.

FIG. 2 shows a cross-sectional view of a non-occluding catheter of FIG. 1 illustrating the relative positions of the distributor 18, the expansion mechanism 20, and the fluid inlet 22, as well as the sheath casing 16.

Figure 3A:
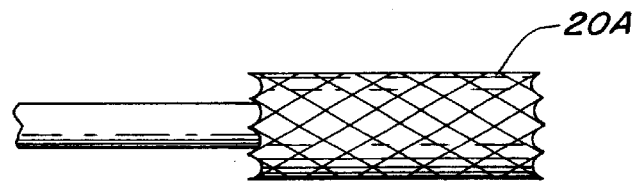
FIG. 3A is a side view of an expansion mechanism according to the invention, in a contracted state.
Figure 3B:
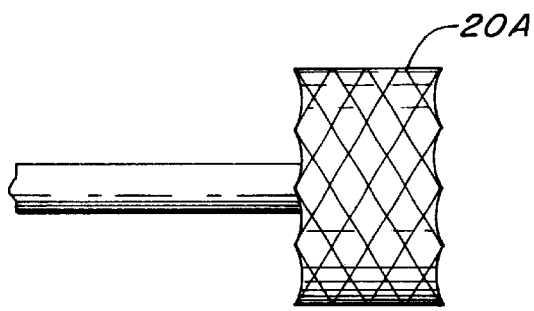
FIG. 3B is a side view of the expansion mechanism of FIG. 3A in an expanded state.

FIGS. 3A and 3B are side views of an expansion mechanism 20A, in a contracted state and expanded state, respectively.

Figure 4:
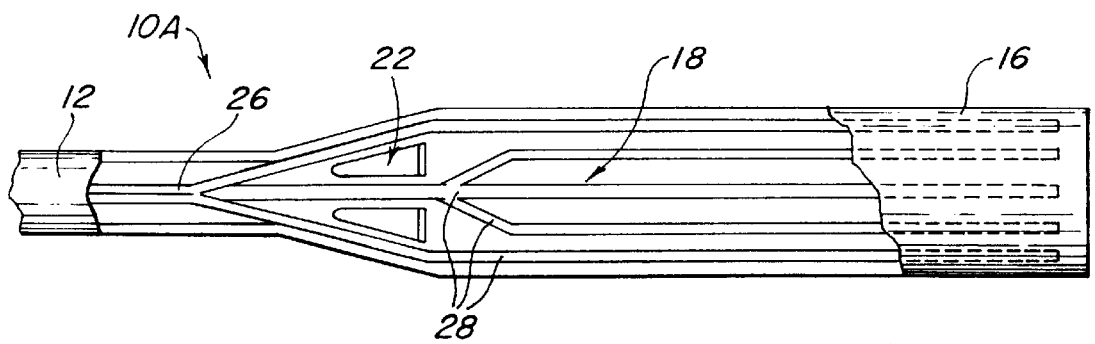
FIG. 4 is a partially cut-away, side view of another non-occluding catheter according to the invention.

FIG. 4 is a partially cut-away view of another non-occluding catheter 10A, having an elongated hollow tube 12, a sheath 16 and a waveguide 26. The waveguide is joined to a distributor 18 that is formed as a branched energy distribution structure 28 within the sheath 16. The distribution array 28 and sheath 16 are expandable to bring the diffuser into close proximity with the vessel wall while creating at least one fluid passageway 22 through the distributor 18.

Figure 5:
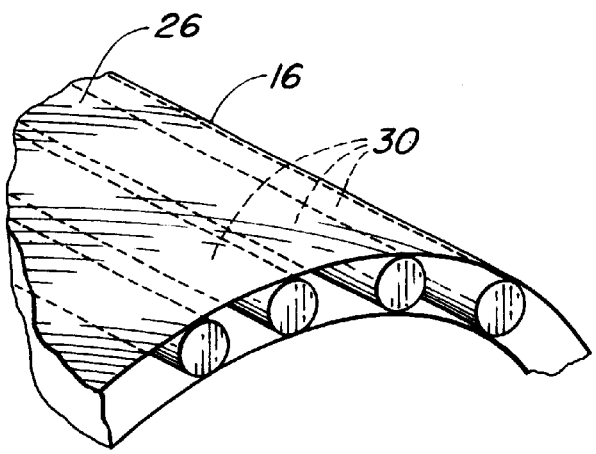
FIG. 5 is a partial view of a sheath and a plurality of distribution elements encased therein.

FIG. 5 is a cross-sectional view of a plurality of light distributing diffusers 30, surrounded by a sheath casing 16. Each diffuser receives energy transmitted from an energy source via the waveguide 26.

Figure 6B:
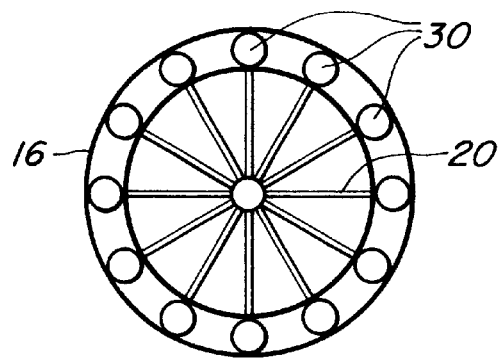
FIG. 6B is a cross-sectional view of an energy distributor in an expanded state.
Figure 6A:
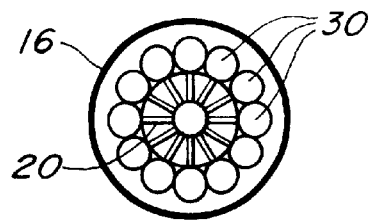
FIG. 6A is a cross-sectional view of an energy distributor in a contracted state.

FIGS. 6A and 6B are cross-sectional views of the plurality of diffusers 30, within a sheath casing 16, surrounding the expansion mechanism 20, in the contracted state and expanded state, respectively.

Figure 7A:
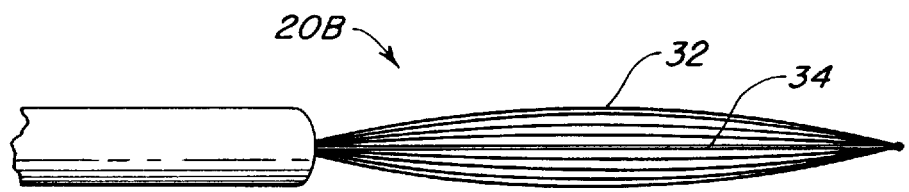
FIG. 7A is a side view of another expansion mechanism in a contracted state.
Figure 7B:
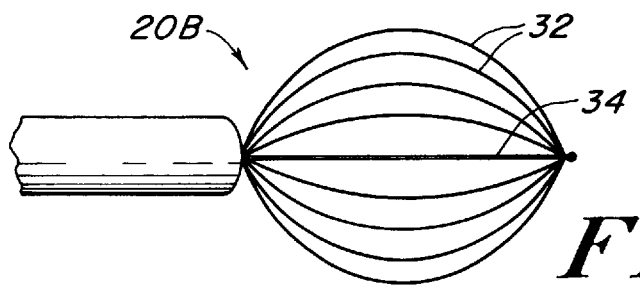
FIG. 7B is a side view of the mechanism of FIG. 7A in an expanded state.

FIGS. 7A and 7B are side views of an alternative expansion mechanism 20B in a contracted state and an expanded state, respectively. In the illustrated embodiment expansion of cage wires 32 can be induced by retraction of a control pull wire 34.

Figure 8A:
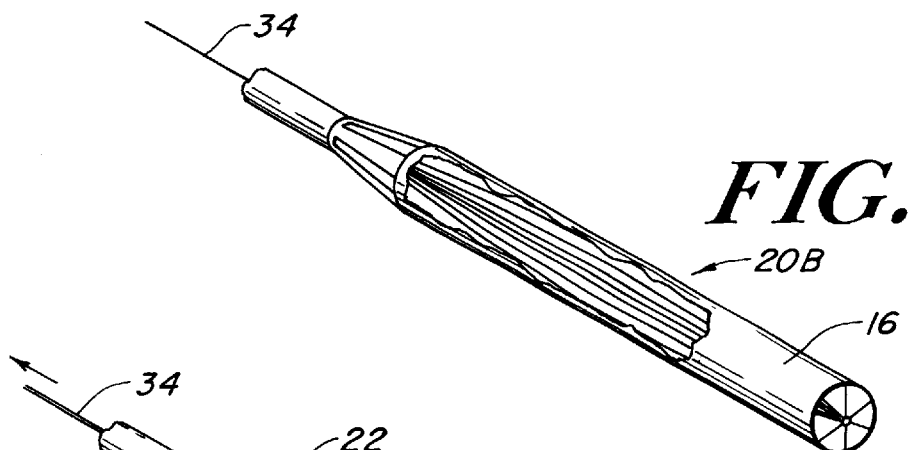
FIG. 8A is a partially, cut-away perspective view of another non-occluding catheter according to the invention in a contracted state.
Figure 8B:
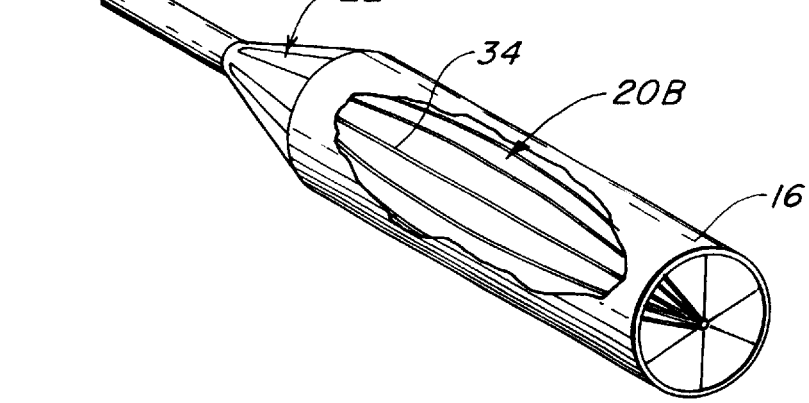
FIG. 8B is a similar perspective view of the catheter of FIG. 8A in an expanded state.

FIGS. 8A and 8B are partially cut away side views of the expansion mechanism 20B, within a sheath casing 16 in a contracted state, and an expanded state, respectively. In the expanded state of FIG. 8B, the expansion mechanism 20B, creates a fluid passageway 22 that permits fluid 24, to pass through the catheter.

Figure 9A:
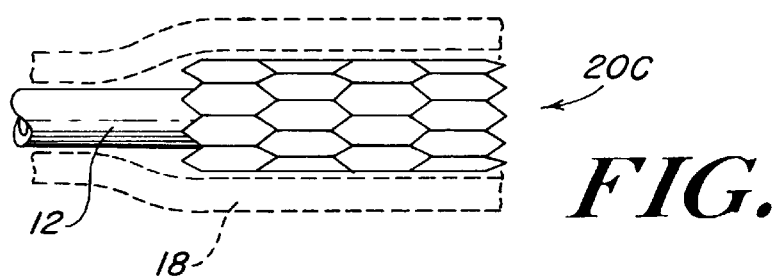
FIG. 9A is a side view of another expander in a contracted state.
Figure 9B:
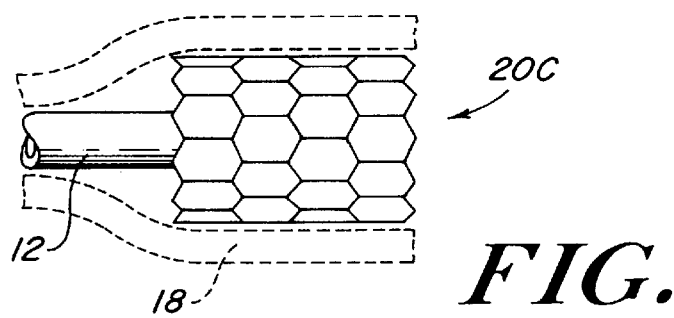
FIG. 9B is a side view of the expander of FIG. 9A in an expanded state.

FIGS. 9A and 9B are side views of a shape memory expansion mechanism 20C, connected to a catheter body 12 and being surrounded by the distributor 18 (shown in phantom), in a contracted state and an expanded state, respectively. Various shape memory materials can be employed in the present invention. For further details on the manufacturing of shape memory devices, see, for example, U.S. Pat. Nos. 4,631,094; 5,540,712 and 5,573,508, incorporated herein by reference.

Figure 10:
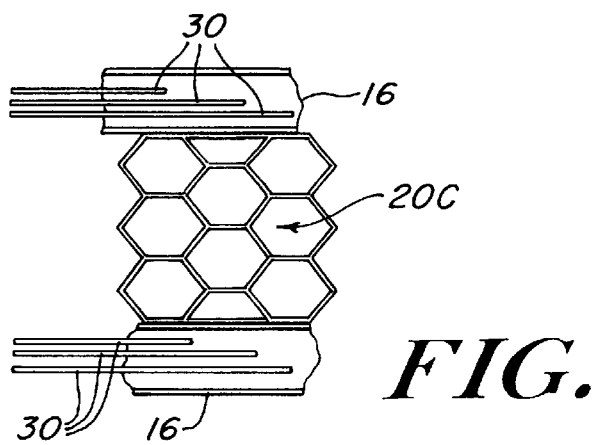
FIG. 10 is a cross-sectional view of an expander in an expanded state together with a surrounding distributor.

FIG. 10 is a cross-sectional side view of one embodiment of the invention, with an expansion mechanism 20C, surrounded by a plurality of diffusers 30, within a sheath casing 16.

Figure 11:
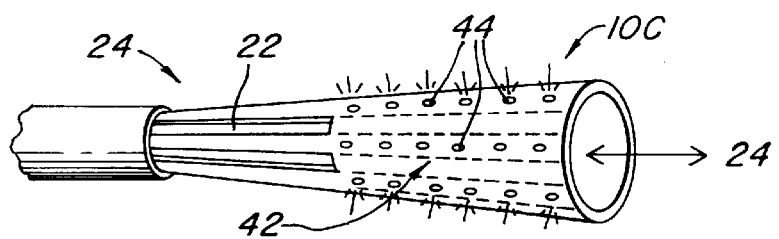
FIG. 11 is a cross-sectional view of fluid flow in a non-occluding catheter according to the invention.

FIG. 11 is a cross-sectional view of the fluid flow 24, through the fluid inlet 22, of another non-occluding catheter 10C according to the invention. FIG. 11 also illustrates an additional feature of the invention that facilitates flushing of the region between the distributor and the target site. Introduction of a flushing medium may be desirable, for example, to clean blood. Alternatively, it may be desirable to administer a local photoactive or other therapeutic agent via a fluid medium. Thus, the embodiment 10C of FIG. 11 provides one or more fluid conduits 42 and at least one port 44 to release fluids at a site. Various devices and techniques for intralumenal irrigation or blood flushing are known. See, for examples, U.S. Pat. Nos. 5,833,682; 5,964,751 and 5,876,426, herein incorporated by reference.

To use the non-occluding catheter, the catheter is first introduced into the lumen of the vessel at a position adjacent to the target region, e.g. an aneurysm, an atherosclerotic plaque, a stenotic lesion, and the like. The expansion mechanism 20, 20A, 20B or 20C, is activated which causes the distributor 18, to come into close proximity with the wall of the lumen.

Following expansion, energy from an energy source is delivered via the waveguide 26, comprising one or more optical fibers, to the diffuser or distribution elements 28. In one embodiment, the distributor elements can be formed of a thin-walled, tube-like flexible material. The distributor can be made of Teflon® P.F.A. materials (polytetrafluoroethylene polymers with perfluoroalpoxy side chains); Teflon® PTFE (polytetrafluoroethylene) and other fluoropolymers. The sheath 16 can be formed of a low-friction, flexible material, e.g., F.E.P., however polyurethane, silicone, polyethylene, or other similar materials may be substituted for PTFE, C-flex, a styrene ethylene butylene styrene block copolymer, and can be simultaneously stretched and slipped over and around the diffuser.

In one embodiment, the distributor is a light diffuser comprising one or more light delivery tubes. The light diffuser can have light scattering material which directs light to the walls of the light diffuser. Examples of a scattering material include, but are not limited to, silicone, epoxy or other polymeric material, or suitable liquid such as water or deuterium oxide solution containing colloidal scatter particles. Optionally, individual light scattering particles may also be included in the light scattering material, such as silica, alumina, and titania or mixtures thereof. In another embodiment, the light scattering material is coated on the inside wall of the light diffuser. Alternatively, the invention can be practiced without the need for an external energy source or waveguide by deploying one or more sources of radiation within the distributor. Such radiation sources can be, for example, liquid radioisotopes or solid radiative pellets.

The arrangement of the distribution elements is such that the distributor can expand and contract in response to the expansion mechanism. A single tube can be arranged, for example, in a helical configuration surrounding the expansion mechanism. Alternatively a branched network can be contracted.

In another embodiment, the energy distributor comprises a plurality of heat conductive tubes arranged around the expansion mechanism. In yet another embodiment the distributor can be a large area resistive heater including one or more heating elements connected to an electric current source.

In each instance, energy is transmitted through the distributor and transferred to the walls of the vessel, without occluding blood flow through the vessel.

The energy source can be any source required to be delivered to a target site. Examples of an energy source include, but are not limited to, light and heat. The source can be a UV light source having a wavelength ranging from about 200 to about 400 nanometers, preferably from about 240 to about 370 nanometers. The radiation can be provided from a variety of sources; including non-coherent UV light sources (e.g., a LF excimer laser operating at 248 nanometers or an Argon ion laser at 257 or 275 nanometers.

Optionally, a therapeutic agent can be used in lieu of, or in combination with, an energy source to treat a target region. The therapeutic agent can be delivered through the distributor topically. Therapeutic agents can also be coated to the exterior surface of the diffuser. In an expanded state, the diffuser would come into close contact with the vessel wall and deposit the therapeutic agent at the target region.

The skilled artisan will appreciate that the expansion mechanism can be any mechanism that pushes the diffuser against the vessel wall while permitting the flow of fluid (e.g., blood, serum, plasma) through the vessel. The expansion mechanism provides structural support in the diffuser. Preferably, the expansion mechanism traverses a major portion of the diffuser to provide structural support and to maintain the shape of the diffuser when inserted in the vessel.

In one embodiment, the expansion mechanism is a flexible spring. The spring can be formed from a continuous piece of fine gauge stainless steel spring wire that, if opened out, would appear in the shape of a zig-zag with multiple elbows. (See, e.g., U.S. Pat. No. 5,855,565 issued to Bar-Cohen et al.) These elbows may be simple arches or recurved arches. The advantage of simple arches is that the spring expands more evenly. The advantage of the recurved arches is that they collapse more readily and are more durable. The spring may be constructed out of inert metals such as titanium, or a plastic. When expanded, the spring can be circular in shape when viewed from above, and may have a diameter smaller than the diameter of the blood vessel lumen when in a contracted state.

In another embodiment, the expansion mechanism is a coil that is inherently flexible and returns to its original shape after being manipulated during insertion into the vessel. In other embodiments, a braid, mesh, or other rigid structures, such as a tube or cylinder may also be used.

The manufacture of the coil may be achieved by embedding the coil into an elastomer or other fluid impermeable flexible material. The elastomer can be drawn over a wire and subsequently shrunk onto the coil, i.e., by heat treatment. The coil can be formed from several materials, for example, stainless steel, tungsten, aluminum and the like. Additionally, a synthetic coil can be formed from Kevlar and like materials. When expanded, the coil can be helical in shape, and may have a diameter less than the diameter of the blood vessel lumen when in a contracted state.

The expander may be self-expanding or, may be activated to expand using a control mechanism, for example, a cable mechanism which causes expansion and contraction of an expander, as described in U.S. Pat. No. 5,855,565 issued to Bar-Cohen et al.

The expansion mechanism can also be one that is expandable out of and retractable back into the elongated hollow instrument. In one embodiment, the expansion mechanism can be radially compressed into a pre-loaded condition within the hollow instrument of the catheter prior to expansion within the vessel lumen. Once proper positioning and alignment of the catheter is achieved, the expansion mechanism is released to allow it to expand radially outward and conform with the interior surface of the vessel.

In other alternative embodiments, various configurations of flexible springs and/or coils are employed as the basic expansion mechanism. The coils generally are provided with a loose or compliant cover, for example, a fluid-impermeable, flexible elastomer material. In some embodiments the coil diameter is controlled by the application of a force to a thread, thin wire or the like, which force in turn alters a natural state of the coil to a contracted state.

The expansion mechanisms can comprise springs or coils designed to exert radially outward with a force of approximately 240 to 340 grams into conforming fixed engagement with the interior surface of the target region. The wire of the spring may be coated with titanium oxide to improve biocompatibility and reduce the incidence of allergic reaction.

One of the most important aspects of the invention is that the catheter does not occlude the flow of blood, but enables blood to pass through the catheter during the entire procedure. The non-occluding catheter does not need to rely upon inflation for expansion, but rather can be mechanically expandable in a way that enables precise control of the amount and speed of expansion during use. As the non-occluding catheter does not restrict the flow of fluid (e.g., blood) at anytime, more time is available to treat the target region compared to conventional techniques.

The non-occluding catheter of the invention is of a size to fit comfortably within an arterial vessel, and is of an overall length and diameter usually in accord with a vessel and permits the flow of blood. The non-occluding catheter is flexible enough to be placed within a moving vessel without damaging the vessel or the surrounding tissues, and is structurally durable enough to maintain a shape permitting the flow of blood.

The non-occluding catheter of the invention can be used for a variety of therapeutic purposes. One application is photodynamic therapy (PDT), a form of light activated chemotherapy. In this approach, photosensitive agents are delivered to the target region. When the cells of the target region have taken up the photosensitive agent, the target region can be irradiated with an appropriate wavelength using the non-occluding catheter of the invention. A photochemical reaction occurs that yields radicals (usually singlet oxygen) which causes metabolic changes in the cell. One advantage of the present invention is that it permits PDT at treatment sites without compromising blood flow at these sites.

The invention also encompasses the use of heat based therapy. For example, heat-based therapy can be used to heat lesions, such as atherosclerotic plaques in a vessel. As the fluid in the vessel is not occluded during treatment, the heat therapy can be applied for longer periods of time.

The non-occluding catheter of the present invention can also be used to deliver drugs or therapeutic agents to the walls of a lumen or vessel. Examples of drugs or agents which can be delivered include substances which inhibit platelet deposition and thrombus formation, or promote thrombolysis and thrombus dissolution, such as plasmin, tissue plasminogen activator (tPA), single chain prourokinase (scuPA), prostaglandins, cyclooxygenase inhibitors, phosphodiesterase inhibitors, thromboxane synthetase inhibitors; antagonists of glycoprotein receptors including (GP) Ib, GP IIb/IIIa, antagonists of collagen receptors, and antagonists of platelet thrombin receptors.

Examples of anticoagulants which can be delivered by the non-occluding catheter include heparin, hirudin, hirulog, hirugen, activated and non-activated protein C, synthetic or naturally occurring antagonists of thrombin, and Factor Xa, or other activated or non-activated coagulation protease inhibitors and coagulation factors, e.g., FIX, FVIII, FV, FVIIa and tissue factor.

Examples of antiproliferatives which can be delivered by the non-occluding catheter include dexamethasone, growth factor, a growth factor inhibitor, growth factor receptor antagonist, transcriptional repressor, translational repressor, antisense DNA, antisense RNA, replication inhibitor, inhibitory antibodies, antibodies directed against growth factors or their receptors, bifunctional molecules comprising a growth factor and a cytotoxin, bifunctional molecules comprising an antibody and a cytotoxin.

The drugs or therapeutic agents delivered by the non-occluding catheter can also be vasodilators, such as nitroglycerin, nitroprusside or other nitric oxide liberators. The vasodilator can also include other suitable vasoactive agents such as beta receptor blocking drugs, inhibitors of intracellular calcium transport, prostaglandins, thromboxane antagonists, and the like.

The non-occluding catheter can also be used for cardiovascular applications which include the delivery of medical grade cyanoacrylides for the treatment of aneurysms, arterial venous fistulas, or carotid cavernous fistulas.

What is claimed is:

1. A catheter for applying energy to a wall of a vessel without occluding fluid flow comprising:
   a hollow elongated instrument having a proximal end and a distal end at least one lumen therethrough, further comprising at least one waveguide disposed within the lumen, the waveguide having a proximal end and a distal end, the proximal end of the waveguide being adapted to receive energy from an energy source;
   a distributor disposed of at the distal end of the instrument constructed to receive energy from the waveguide and distribute the energy into a target region of a vessel wall; and an expansion mechanism connected to the distributor for expanding the energy distributor at the target region in order to bring the distributor into close proximity with the vessel wall while creating at least one fluid passageway through the distributor.

2. The catheter of claim 1, wherein the waveguide comprises at least one optical fiber.

3. The catheter of claim 1, wherein the waveguide comprises at least one electrical conductor.

4. The catheter of claim 1, wherein the waveguide comprises at least one thermal conductor.

5. The catheter of claim 1, wherein the distributor is a light distributor comprising at least one light diffuser.

6. The catheter of claim 5, wherein the light diffuser further comprises a light scattering material which directs light to the walls of the light diffuser.

7. The catheter of claim 6, wherein the light scattering material further comprises a polymeric material which has light scattering particles dispersed therein.

8. The catheter of claim 7, wherein the light scattering particles are selected from the group consisting of alumina, silica, and titania compounds and mixtures thereof.

9. The catheter of claim 6, wherein the light scattering material is coated on the inner side of the light diffuser.

10. The catheter of claim 1, wherein the distributor further comprises a sheath casing.

11. The catheter of claim 1, wherein the expansion mechanism comprises a flexible spring expander.

12. The catheter of claim 1, wherein the expansion mechanism comprises a coil expander.

13. The catheter of claim 1, wherein the expansion mechanism a shape-memory material.

14. The catheter of claim 1 wherein the catheter further comprises at least one conduit for a fluid medium and at least one port on the distributor to release the fluid medium.

15. The catheter of claim 1, further comprising a control mechanism to activate the expansion mechanism from a contracted state to an expanded state.

16. A method for delivering energy to the walls of a vessel without occluding fluid flow comprising:
    inserting a catheter into the lumen of the vessel, the catheter comprising an elongated hollow instrument having a proximal end and distal end and further comprising a waveguide disposed within the lumen, the waveguide having a proximal end and a distal end, the proximal end of the waveguide being adapted for receiving energy from an energy source and delivering energy to the interior of, a distributor at the distal end of the waveguide, the distributor being constructed for receiving energy from the waveguide and for distributing energy to a target region of a vessel wall, and an expansion mechanism connected to the energy distributor for expanding the distributor at the target region;
    activating the expansion mechanism, thereby expanding the energy distributor at the target region and creating at least one fluid passageway through the distributor; and
    transmitting the energy from the distributor to the target region.

17. The method of claim 16, wherein the step of delivering energy further comprises irradiating with light.

18. The method of claim 16, wherein the step of delivering energy further comprises transmitting phototherapeutic radiation via a plurality of optical fibers.

19. The method of claim 16, wherein the method further comprises delivering energy to a vessel to treat a region.

20. The method of claim 19, further comprising treating a region wherein the region is an aneurysm.

21. The method of claim 19, further comprising treating a region wherein the region is an atherosclerotic plaque.

22. The method of claim 16, wherein the step of transmitting energy further comprises irradiating the target region with light.

23. The method of claim 16, wherein the step of transmitting energy further comprises heating or cooling a target region.

24. A method for treating a region in a vessel without occluding fluid flow comprising:
    administering a therapeutically effective amount of a therapeutic agent to the subject;
    inserting a catheter into the lumen of the vessel, the catheter comprising an elongated hollow instrument having a proximal end and distal end and further comprising a waveguide disposed within the lumen, the waveguide having a proximal end and a distal end, the proximal end of the waveguide being adapted for receiving energy from an energy source and delivering energy to the interior of, a distributor at the distal end of the waveguide, the distributor being constructed for receiving energy from the waveguide and for distributing energy to a target region of a vessel wall, and an expansion mechanism connected to the energy distributor for expanding the distributor at the target region;
    activating the expansion mechanism, thereby expanding the energy distributor at the target region and creating at least one fluid passageway through the distributor; and
    transmitting energy to the target region via the distributor that modulates the therapeutic agent such that the therapeutic agent alters the target region, thereby treating the region.

25. The method of claim 24, further comprising treating a region wherein the region is an aneurysm.

26. The method of claim 24, further comprising treating a region wherein the region is an atherosclerotic plaque.

27. The method of claim 24, wherein the step of administering a therapeutic agent comprises administering a therapeutic agent selected from the group consisting of a photoactivatable agent and a thermoactivatable agent.

28. The method of claim 24, wherein the step of administering further comprises systemically administering the therapeutic agent.

29. The method of claim 24, wherein the step or administering further comprises locally administering the therapeutic agent.

30. The method of claim 24, wherein the stop of delivering energy further comprises irradiating with light.

31. The method of claim 24, wherein the step of transmitting energy further comprises heating the region.

32. The method of claim 24, wherein the step of transmitting energy further comprises cooling the region.

33. A catheter for applying energy to a wall of a vessel without occluding fluid flow comprising:
    a hollow elongated instrument having a proximal end and a distal end;
    a distributor disposed of at the distal end of the instrument, wherein the distribute comprises a source of ionizing radiation, and is constructed to distribute the radiation into a target region of a vessel wall; and
    an expansion mechanism connected to the distributor for expanding the distributor at the target region in order to bring the distributor into close proximity with the vessel wall while creating at least one fluid passageway through the distributor.

34. The catheter of claim 33, wherein the source of ionizing radiation is a liquid radiation source.

35. The catheter of claim 34, wherein the liquid radiation source is a liquid radioisotope.

36. The catheter of claim 33, wherein the source of ionizing radiation is a solid radiation source.

37. The catheter of claim 36, wherein the solid radiation source is a radioactive pellet.

38. The catheter of claim 33, wherein the distributor further comprises a sheath casing.

39. The catheter of claim 33, wherein the expansion mechanism comprises a flexible spring expander.

40. The catheter of claim 33, wherein the expansion mechanism comprises a coil expander.

41. The catheter of claim 33, wherein the expansion mechanism a shape-memory material.

42. The catheter of claim 33, wherein the catheter further comprises at least one conduit for a fluid medium and at least one port on the distributor to release the fluid medium.

43. The catheter of claim 33, further comprising a control mechanism to activate the expansion mechanism from a contracted state to an expanded state.

44. A method for delivering energy to the walls of a vessel without occluding fluid flow comprising:

inserting a catheter into the lumen of the vessel, the catheter comprising an elongated hollow instrument having a proximal end and distal end, and a distributor comprising a source of ionizing radiation, wherein the distributer is constructed to distribute the radiation to a target region of a vessel wall, and an expansion mechanism connected to the radiation distributor for expanding the distributor at the target region;

activating the expansion mechanism, thereby expanding the energy distributor at the target region and creating at least one fluid passageway through the distributor; and transmitting the radiation emitted by the source of ionizing radiation from the distributor to the target region.

45. The method of claim 44, wherein the method further comprises delivering energy to a vessel to treat a regions.

46. The method of claim 44, further comprising treating a region wherein the region is an aneurysm.

47. The method of claim 44, further comprising treating a region wherein the region is an atherosclerotic plaque.

48. A method for treating a region in a vessel without occluding fluid flow comprising:

administering a therapeutically effective amount of a therapeutic agent to the subject;

inserting a catheter into the lumen of the vessel, the catheter comprising an elongated hollow instrument having a proximal end and distal end, and a distributor comprising a source of ionizing radiation, wherein the distributer is constructed to distribute the radiation to a target region of a vessel wall, and an expansion mechanism connected to the radiation distributor for expanding the distributor at the target region;

activating the expansion mechanism, thereby expanding the energy distributor at the target region and creating at least one fluid passageway through the distributor; and transmitting the radiation emitted by the source of ionizing radiation to the target region via the distributor that modulates the therapeutic agent such that the therapeutic agent alters the target region, thereby treating the region.

49. The method of claim 48, further comprising treating a region wherein the region is an aneurysm.

50. The method of claim 48, further comprising treating a region wherein the region is an atherosclerotic plaque.

51. The method of claim 48, wherein the step of administering a therapeutic agent comprises administering a therapeutic agent selected from the group consisting of a photoactivatable agent and a thermoactivatable agent.

52. The method of claim 48, wherein the step of administering further comprises systemically administering the therapeutic agent.

53. The method of claim 48, wherein the step or administering further comprises locally administering the therapeutic agent.

54. The method of claim 48, wherein the step of transmitting the radiation emitted by the source of ionizing radiation further comprises heating the region.

55. The method of claim 48, wherein the step of transmitting the radiation emitted by the source of ionizing radiation further comprises cooling the region.

* * * * *